(12) United States Patent
Pizzini

(10) Patent No.: US 9,283,343 B2
(45) Date of Patent: Mar. 15, 2016

(54) NASAL CANNULA ADAPTER

(75) Inventor: Mark-Alan Pizzini, Wynnewood, PA (US)

(73) Assignee: Institute for Cancer Research, Philadelphia, PA (US)

( * ) Notice: Subject to any disclaimer, the term of this patent is extended or adjusted under 35 U.S.C. 154(b) by 341 days.

(21) Appl. No.: 13/988,797

(22) PCT Filed: Nov. 22, 2011

(86) PCT No.: PCT/US2011/061823
§ 371 (c)(1),
(2), (4) Date: May 22, 2013

(87) PCT Pub. No.: WO2012/071398
PCT Pub. Date: May 31, 2012

(65) Prior Publication Data
US 2013/0239970 A1   Sep. 19, 2013

Related U.S. Application Data

(60) Provisional application No. 61/416,392, filed on Nov. 23, 2010, provisional application No. 61/438,715, filed on Feb. 2, 2011, provisional application No. 61/496,636, filed on Jun. 14, 2011.

(51) Int. Cl.
*A61M 16/06* (2006.01)
*A61M 16/04* (2006.01)
*A61M 16/08* (2006.01)

(52) U.S. Cl.
CPC ....... *A61M 16/0666* (2013.01); *A61M 16/0463* (2013.01); *A61M 16/0672* (2014.02); *A61M 16/0816* (2013.01); *A61M 16/0683* (2013.01)

(58) Field of Classification Search
CPC ............ A61M 16/0057; A61M 16/04; A61M 16/0461; A61M 16/0463; A61M 16/0465; A61M 16/0666; A61M 16/0672; A61M 16/0677; A61M 16/0683; A61M 16/0816; A61M 2202/0208; A61M 39/1011; A61M 39/12; A61M 2039/1027
USPC ............ 128/200.24, 200.26, 202.27, 203.22, 128/204.18, 205.22, 205.25, 206.11, 128/206.12, 206.18, 206.21, 206.27, 128/206.29, 207.13–207.15, 207.18, 912, 128/DIG. 26
See application file for complete search history.

(56) References Cited

U.S. PATENT DOCUMENTS 3,730,179 A * 5/1973 Williams .......... A61M 16/0463
128/204.18
3,915,173 A * 10/1975 Brekke ........... A61M 17/12022
128/207.15

(Continued)

FOREIGN PATENT DOCUMENTS

WO   WO 2008142359 A1 * 11/2008 ............ A61M 16/00

OTHER PUBLICATIONS

International Search Report and Written Opinion issued for PCT/US2011/061823 dated Feb. 29, 2012.

*Primary Examiner* — Tan-Uyen (Jackie) T Ho
*Assistant Examiner* — Joseph D Boecker
(74) *Attorney, Agent, or Firm* — Stradley Ronon Stevens & Young, LLP

(57) ABSTRACT

A nasal cannula adapter. The nasal cannula adapter includes a chamber having cannula clips, and a connector having an opening and a connector lumen in communication with the chamber and the opening. Systems for administering a gas to a patient comprise the nasal cannula adapter, a nasal cannula, and an airway device. Methods for administering a gas to a patient comprise administering a gas through a nasal cannula operably connected to the nasal cannula adapter operably connected to an airway device inserted into the airway of the patient.

20 Claims, 13 Drawing Sheets

(56) References Cited

U.S. PATENT DOCUMENTS

| | | | | | |
|---|---|---|---|---|---|
| 4,240,417 | A | * | 12/1980 | Holever | A61M 16/0465 128/203.12 |
| 5,375,593 | A | * | 12/1994 | Press | A61M 16/0666 128/207.18 |
| 5,513,634 | A | * | 5/1996 | Jackson | A61M 16/0666 128/200.26 |
| 5,590,643 | A | * | 1/1997 | Flam | A61M 16/0488 128/200.26 |
| 5,645,046 | A | * | 7/1997 | Kay | A62B 9/06 128/201.18 |
| 2004/0206907 | A1 | * | 10/2004 | Yamamori | A61B 5/0836 250/343 |
| 2004/0221853 | A1 | | 11/2004 | Miller | |
| 2006/0042631 | A1 | * | 3/2006 | Martin | A61B 5/0836 128/207.18 |
| 2006/0130840 | A1 | | 6/2006 | Porat et al. | |
| 2006/0278238 | A1 | * | 12/2006 | Borody | A61B 1/24 128/848 |
| 2007/0068535 | A1 | * | 3/2007 | Colman | A61B 1/00154 128/859 |
| 2009/0095303 | A1 | * | 4/2009 | Sher | A61M 16/06 128/207.18 |
| 2010/0069770 | A1 | | 3/2010 | Girshin et al. | |
| 2010/0262033 | A1 | * | 10/2010 | Colman | A61M 16/0488 600/532 |
| 2010/0317987 | A1 | * | 12/2010 | Inoue et al. | A61M 16/0488 600/543 |

\* cited by examiner

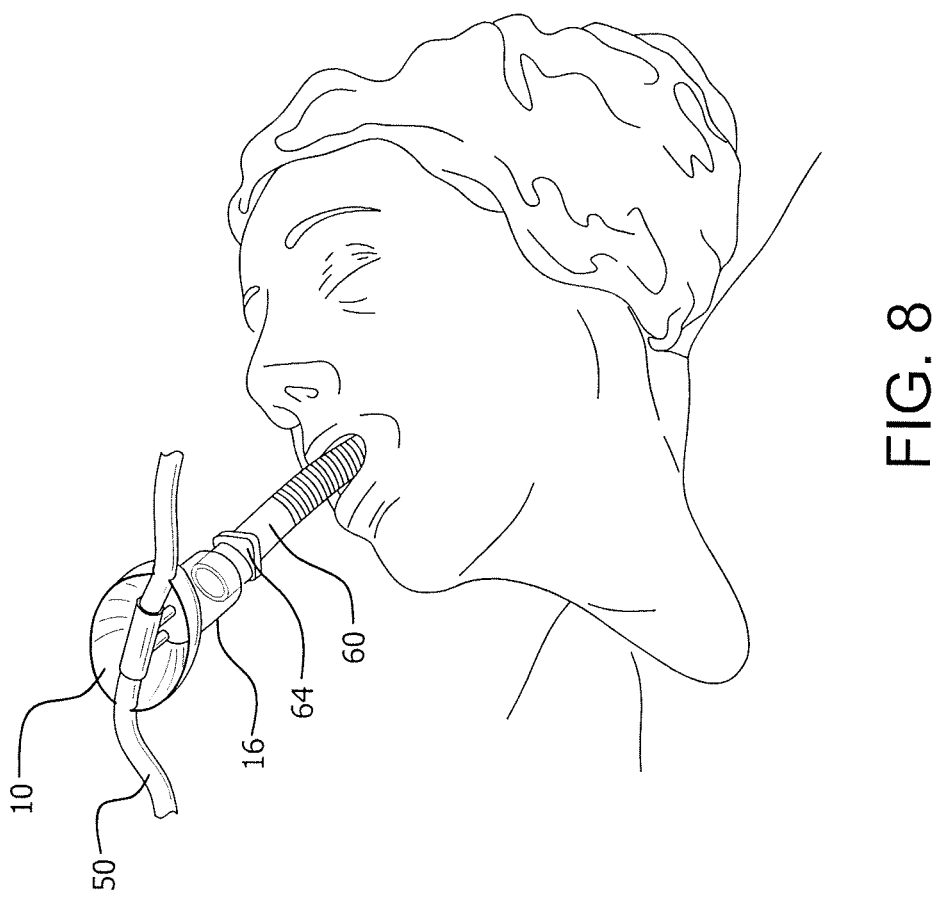

NASAL CANNULA ADAPTER

CROSS REFERENCE TO RELATED APPLICATIONS

This application is the U.S. National Phase of PCT Application No. PCT/US2011/061823, filed on Nov. 22, 2011, and claims priority to U.S. Provisional Application Nos. 61/416,392 filed on Nov. 23, 2010, 61/438,715 filed on Feb. 2, 2011, and 61/496,636 filed on Jun. 14, 2011; the entire contents of each of these applications are incorporated by reference herein, in their entirety and for all purposes.

FIELD OF THE INVENTION

The invention relates generally to the field of medical devices. More particularly, the invention relates to nasal cannula adapters, systems, and methods for delivering supplemental oxygen to patients following a medical procedure in which an airway device is used.

BACKGROUND OF THE INVENTION

Various publications, including patents, published applications, technical articles and scholarly articles are cited throughout the specification. Each of these cited publications is incorporated by reference, in its entirety and for all purposes, in this document.

During surgery, patients are generally administered oxygen or anesthetic gases via a laryngeal mask airway (LMA), endotracheal tube (ETT), or tracheotomy tube placed in the patient's airway. The LMA or ETT is typically removed shortly after the procedure, but it is often necessary to keep the LMA or ETT in place for additional time. While the LMA or ETT remains in place, supplemental oxygen is supplied to the patient through these airway devices, and the supplemental oxygen is required until the airway device is removed. Supplemental oxygen is delivered, for example, via a T-piece connected to a lengthy tube that attaches to an oxygen supply, via a Mapleson-style circuit, or via a tracheotomy collar.

When the airway device is removed, the T-piece or circuit piece is discarded, and additional oxygen may be supplied to the patient via a nasal cannula placed on the patient. Thus, supplying a post-surgical patient with oxygen typically requires a two-step process (e.g., T-piece exchanged for a nasal cannula), which is costly and generates waste. There is a need for less costly and more efficient systems for delivering supplemental oxygen to post-surgical patients.

SUMMARY OF THE INVENTION

The invention features nasal cannula adapters. In some aspects, a nasal cannula adapter comprises a chamber having two cannula clips and a connector in communication with the chamber, with the connector having a connector lumen and an opening in communication with the connector lumen. The connector is preferably adapted to connect the nasal cannula adapter to an airway device. The chamber may optionally be partially enclosed, for example, with a lid. Optionally, the connector further comprises a seal positioned substantially at the opening. Optionally, the nasal cannula adapter comprises an oxygen reservoir.

The cannula clips can each be a hole through the nasal cannula adapter. The cannula clips may each comprise a fastener such as a clasp, clip, clamp, catch, dog, collar, adhesive, grapple, grasp, snare, or hook, and may be separate from or integral with the adapter. The cannula clips may comprise a support such as an arm, wing, bracket, branch, protrusion, extension, stirrup, truss, prop, or other support capable of holding and securing a nasal cannula in place. Combinations of holes, supports, and fasteners may be used.

The inner side walls of the chamber may be shaped to fit a nasal cannula and/or to otherwise hold a nasal cannula in place within the chamber, thereby substantially reducing or preventing undesired rotation of the nasal cannula and maintaining the flow of gas from the nasal cannula toward the patient. The shape may comprise tapering. The inner side walls of the chamber may comprise a berm.

In some preferred aspects, the connector is adapted to fit over the end of the airway device. In some aspects, the connector is adapted to fit inside the end of the airway device. The airway device can be an endotracheal tube, laryngeal mask airway, combitube, or tracheotomy tube.

The nasal cannula adapter may further comprise a bulkhead positioned substantially where the chamber intersects the connector lumen. The bulkhead may comprise two holes through the bulkhead adapted to friction fit nare prongs of a nasal cannula.

The invention also features systems for administering a gas to a patient. In some aspects, a system comprises a nasal cannula adapter, a nasal cannula, and an airway device. Optionally, the system may comprise a gas supply, for example, an oxygen supply. The airway device can be an endotracheal tube, laryngeal mask airway, combitube, or tracheotomy tube.

The invention also features methods for administering a gas to a patient in need thereof. In some aspects, a method comprises administering a gas through a nasal cannula operably connected to a nasal cannula adapter operably connected to an airway device inserted into the airway of the patient. Any gas such as an anesthetic gas or oxygen can be administered, and can be administered at a degree of flow suitable to establish or maintain a desired saturation in the patient. Optionally, the method may comprise removing the nasal cannula from the nasal cannula adapter and placing the nasal cannula on the patient.

It is to be understood that both the foregoing general description and the following detailed description are exemplary, but are not restrictive, of the invention.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures:

FIG. 8 shows a nasal cannula adapter attached to the external end of an airway device that is inserted into the airway of a patient.

DETAILED DESCRIPTION OF THE INVENTION

Various terms relating to aspects of the present invention are used throughout the specification and claims. Such terms are to be given their ordinary meaning in the art, unless otherwise indicated. Other specifically defined terms are to be construed in a manner consistent with the definition provided in this document.

As used throughout, the singular forms "a," "an," and "the" include plural referents unless expressly stated otherwise.

The invention features devices, systems, and methods for administering a gas to a patient in need of that gas. The devices, systems, and methods may find use, for example, in surgery or post-surgery recovery, or during any other medical diagnostic or treatment procedure in which a gas is to be administered to a patient. A foundational feature is a nasal cannula adapter.

The components of the nasal cannula adapter can be fabricated from any suitable material or combination of materials. Materials include plastic, polymers, glass, rubber, metal, and composites, preferably medical or surgical grade.

Figure 1A:
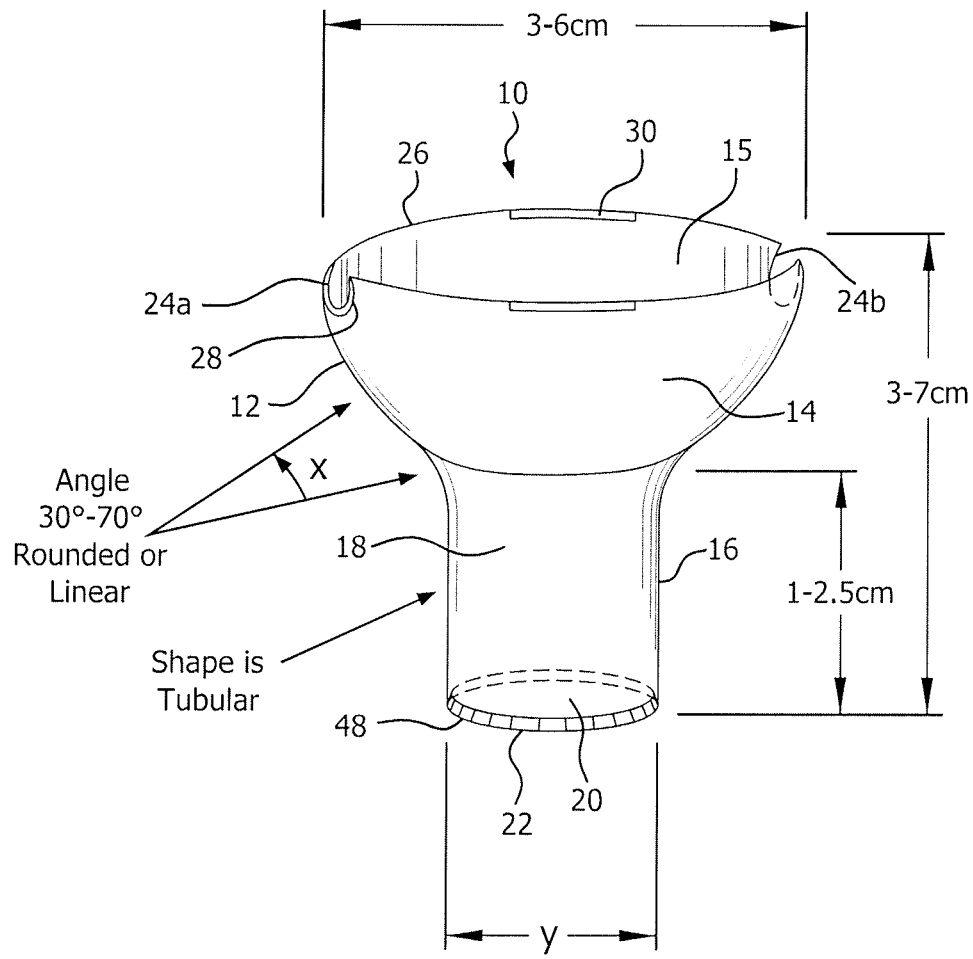
FIG. 1a shows a nasal cannula adapter.

Referring now to the drawings, in which like reference numbers refer to like elements throughout the various figures that comprise the drawings, FIG. 1a shows one non-limiting embodiment of a nasal cannula adapter 10. The nasal cannula adapter 10 has a body 12 that surrounds a chamber 14 and has a connector 16 that can be used to connect the nasal cannula adapter 10 to an airway device such as an endotracheal tube, laryngeal mask airway, or tracheotomy tube. The connector 16 includes a connector lumen 18 in communication with the chamber 14. The chamber 14 has inner side walls 15. The connector 16 has an opening 20 at its distal end 22 that is in communication with the connector lumen 18. Optionally, the distal end 22 may have a seal 48 with a function as described below.

The body 12 has at least one cannula clip 24a or 24b, and preferably two cannula clips 24a and 24b. An embodiment with two cannula clips 24a and 24b is shown in FIG. 1a, with the cannula clips 24a and 24b positioned at the proximal end 26 of the nasal cannula adapter 10. In some preferred aspects, cannula clips 24a and 24b are holes bored through the sidewall of the body 12. In aspects where the chamber 14 of the nasal cannula adapter 10 is enclosed, the cannula clips 24a and 24b may optionally include a seal 28 to prevent the escape of gas from the chamber 14 through the bores. Cannula clips 24a and 24b may also comprise a fastener 72 such as a clasp, clamp, catch, dog, collar, adhesive, grapple, grasp, snare, hook, or other suitable fastener 72 attached to the body 12. During use of the nasal cannula adapter 10, a nasal cannula 50 is inserted into the cannula clips 24a and 24b, which hold the nasal cannula 50 in place.

The cannula clips 24 may also extend out from the body 12. For example, the cannula clips 24 may comprise a support as shown in FIG. 1f. In some aspects, each cannula clip 24a and 24b may comprise a support such as an arm, wing, bracket, branch, protrusion, extension, stirrup, truss, prop, or other support capable of holding and securing the nasal cannula 50 in place on the nasal cannula adapter 10. The support may be separate and connectable/connected to, or may be integral with the body 12, and may extend at any suitable angle and in any suitable direction from the body 12. In aspects where the cannula clips 24a and 24b extend out from the body 12, the cannula clips 24a and 24b may optionally include a seal 28 (see FIG. 1d). Extended cannula clips 24 may also comprise a fastener such as a clasp, clamp, catch, dog, collar, adhesive, grapple, grasp, snare, hook, or other suitable fastener.

Figure 1B:
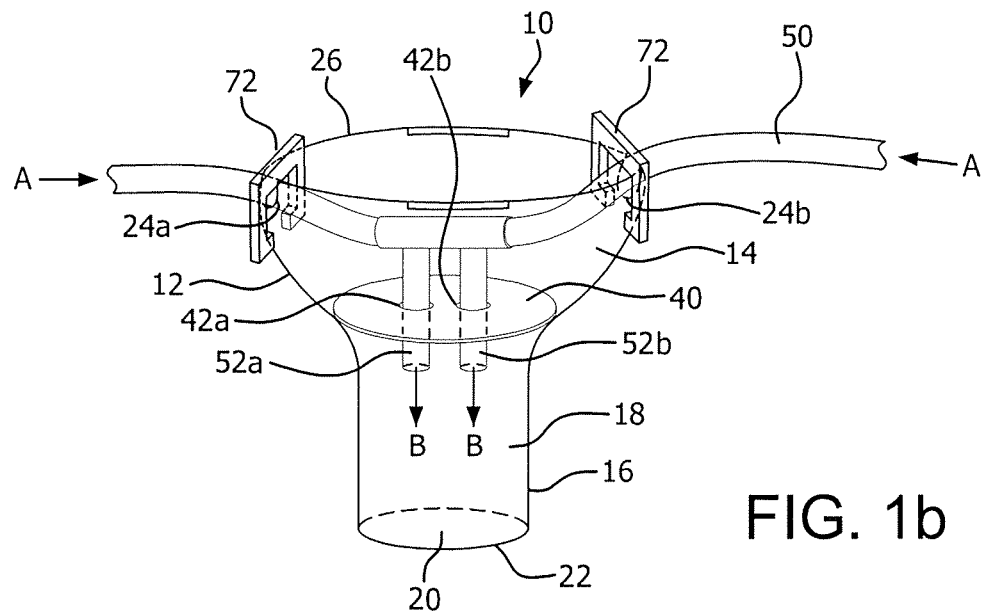
FIG. 1b shows an alternative embodiment of a nasal cannula adapter.

In some aspects, the nasal cannula adapter 10 optionally includes a bulkhead 40, preferably located substantially where the body 12 intersects with the connector 16, for example, as shown in FIG. 1b. The bulkhead 40 preferably has at least two holes 42a and 42b through the bulkhead 40. When a nasal cannula 50 is attached to a nasal cannula adapter 10 including a bulkhead 40, each nare prong 52a and 52b of the nasal cannula 50 can be inserted into the holes 42a and 42b in the bulkhead 40 to allow a gas to flow from the nasal cannula 50 into the connector lumen 18 of the nasal cannula adapter 10. The bulkhead 40 may be a membrane or may be fabricated from the same material as the material of the nasal cannula adapter 10. The bulkhead 40 may include additional valves, holes, slots, or pores to allow gas to pass freely between the connector lumen 18 and the chamber 14, for example, to allow for exhalation. Optionally, the holes 42a and 42b may include a seal to prevent the escape of gas from the connector lumen 18 through the holes 42a and 42b. It is preferred that the nare prongs 52a and 52b engage the holes 42a and 42b of the bulkhead 40 with a friction fit.

In some aspects, the nasal cannula adapter 10 includes shaped inner side walls 15 of the chamber 14. The shapes may comprise tapering, beveling, slanting, narrowing, or other configurations that help to hold a nasal cannula 50 in place. For example, if not secured in place, a nasal cannula 50 may twist or rotate such that nare prongs 52a and 52b point in an undesired direction, and cause the flow of a gas out of the nare prongs 52a and 52b of a nasal cannula 50 to be directed upward or otherwise away from the connector lumen 18 and the patient's airway. As a result, the patient may not receive the proper amount of the gas, for example, oxygen. Thus, the shaping of the inner side walls 15 of the chamber 14 substantially reduces or prevents undesired rotation of the nasal cannula 50, and maintains a maximal flow of a gas downward into the connector lumen 18 and toward the patient.

Figure 5:
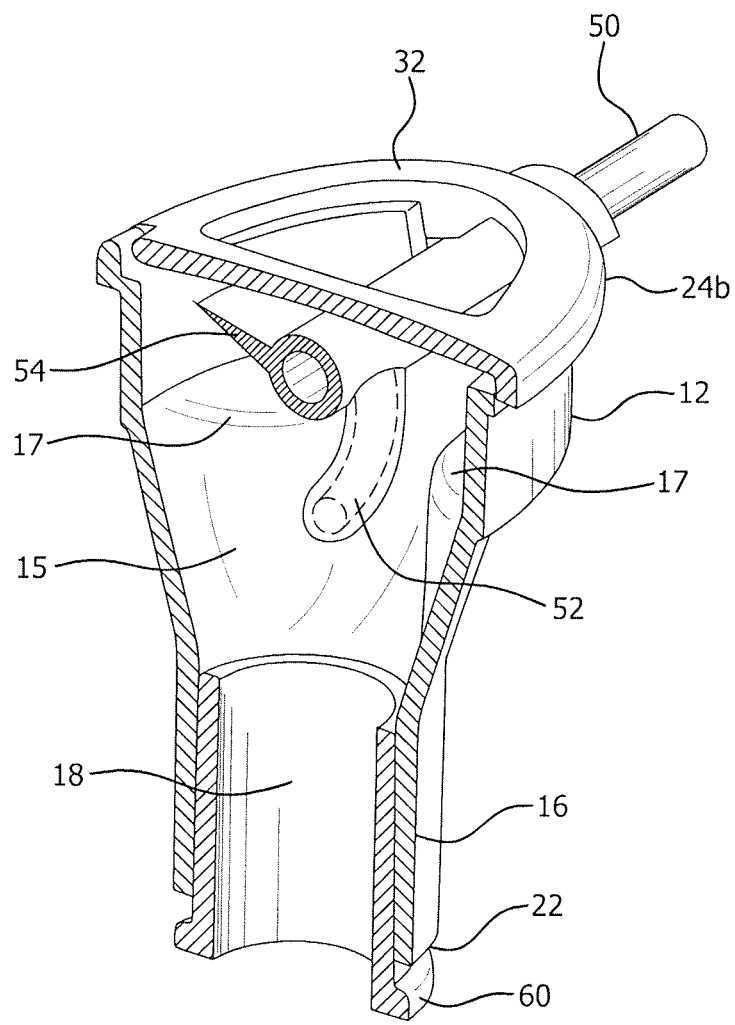
FIG. 5 shows a cut-away view of a nasal cannula adapter showing tapered inner sidewalls of the chamber.
Figure 7A:
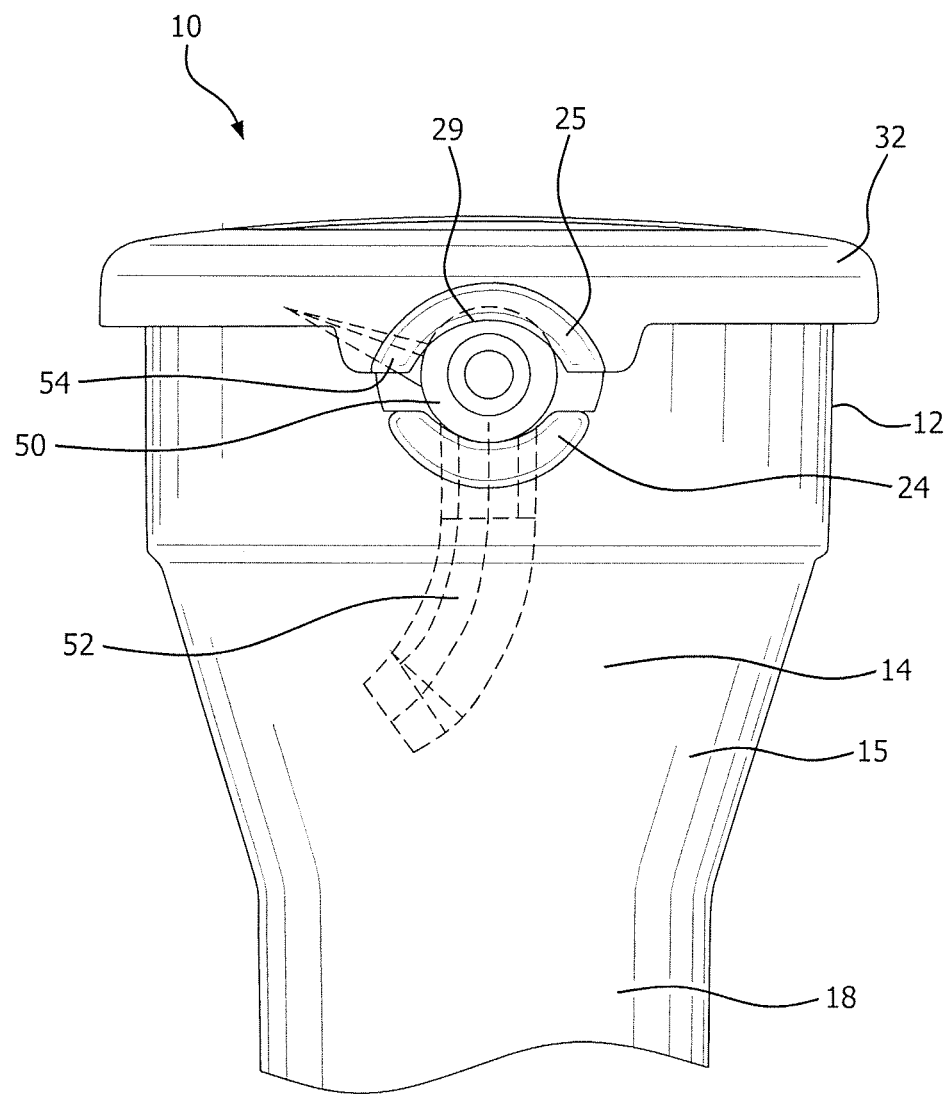
FIG. 7a shows a side-view of a nasal cannula adapter and a nasal cannula.

The inner side walls 15 of the chamber 14 may comprise a shape that mediates contact with the nare prongs 52a and 52b in order to hold them in place within the chamber 14, for example, by way of a friction fit. The thickness and the shape of the inner side walls 15 may vary, for example, to accommodate different types of nare prongs 52a and 52b such as curved nare prongs 52a and 52b, straight nare prongs 52a and 52b, flared nare prongs 52a and 52b, large nare prongs 52a and 52b, small nare prongs, 52a and 52b, and other shapes of nare prongs 52a and 52b available for patient use. FIG. 5 and FIG. 7a show examples of tapering of the inner side walls 15 and how a nare prong 52 may fit within the tapering.

Figure 6:
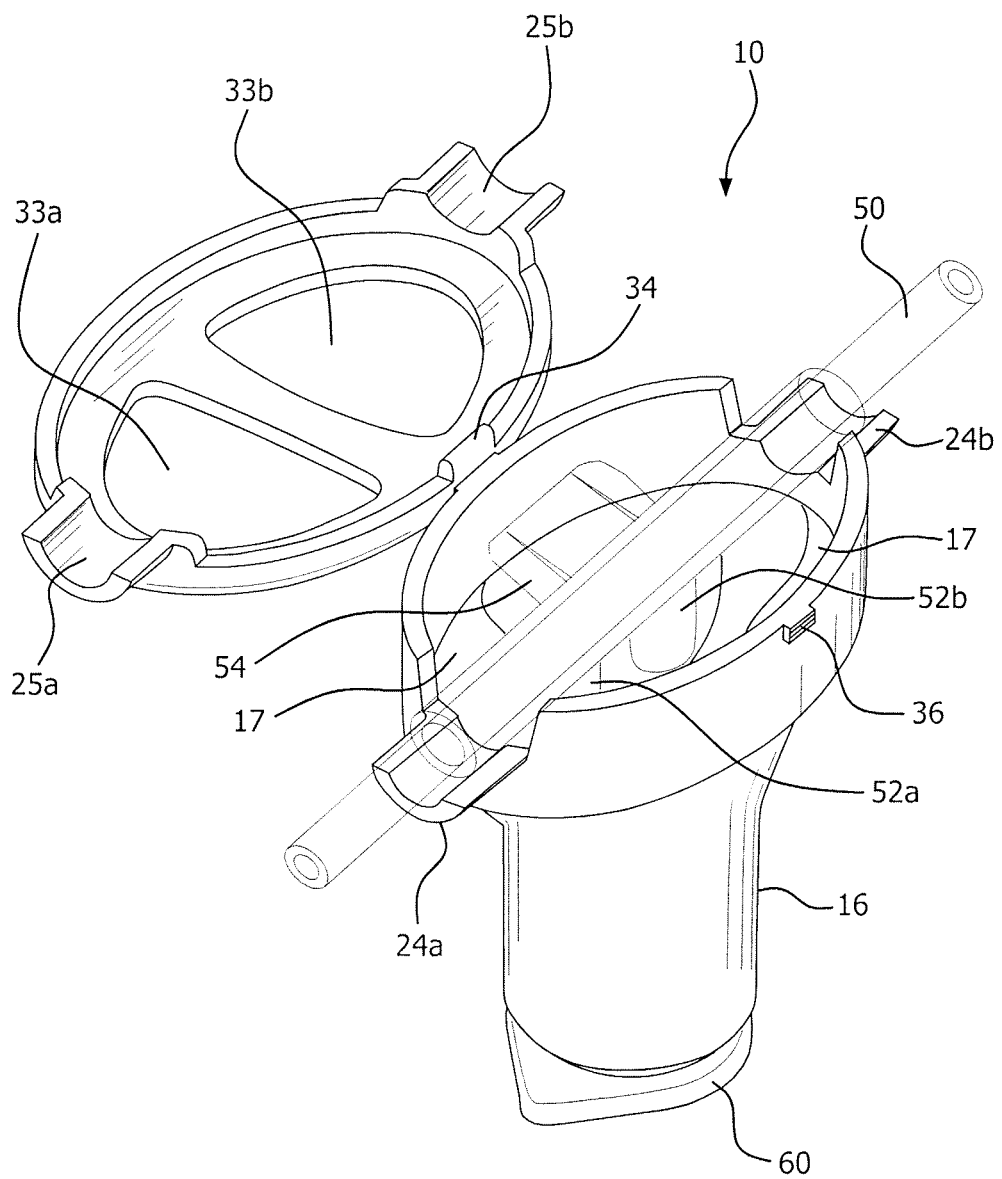
FIG. 6 shows a nasal cannula adapter with tapered inner sidewalls of the chamber and a nasal cannula seated in the adapter.

The inner side walls 15 may comprise a berm or ledge 17. The berm 17 may contact a lip plate 54 of a nasal cannula 50. In contacting a lip plate 54, the berm 17 may reduce or prevent unwanted rotation of the nasal cannula 50. An example of a berm 17 is shown in FIG. 5 and FIG. 6.

Figure 1C:
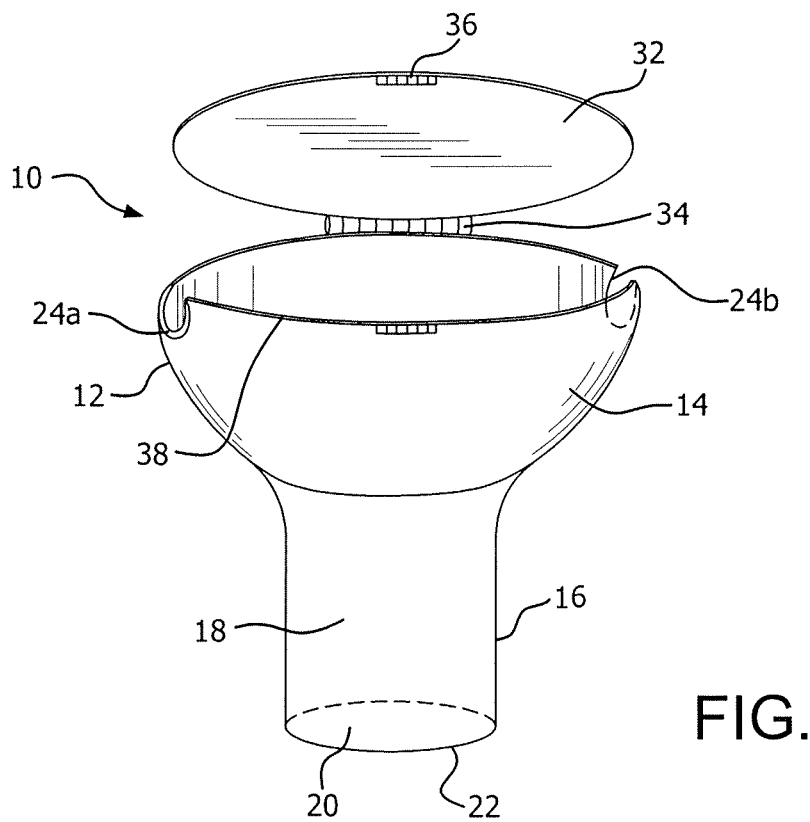
FIG. 1c shows a nasal cannula adapter with a lid.
Figure 1E:
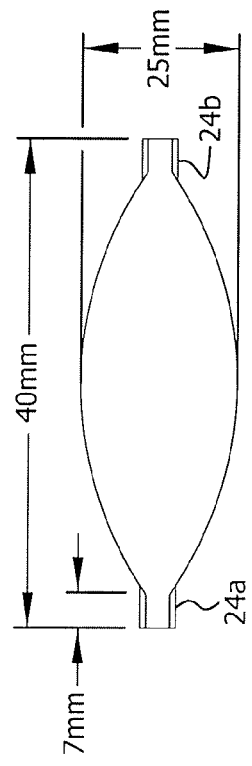
FIG. 1e shows a side view of a cannula clip.
Figure 1F:
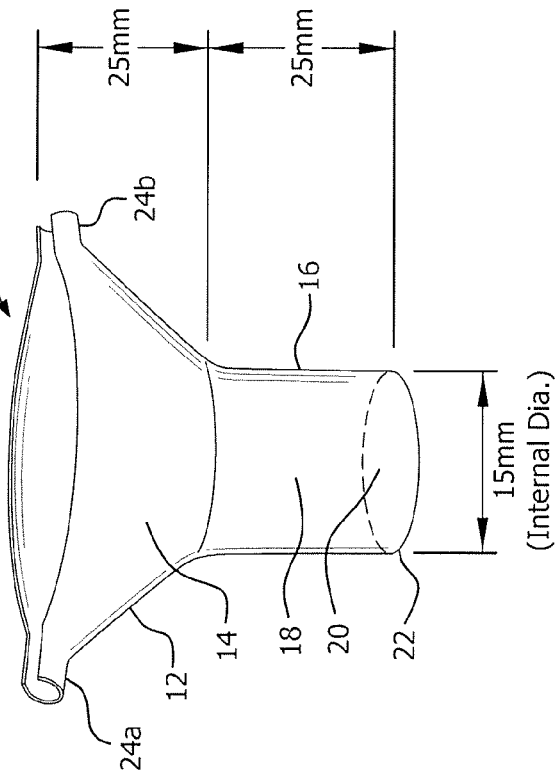
FIG. 1f shows a top view of a nasal cannula adapter.
Figure 1D:
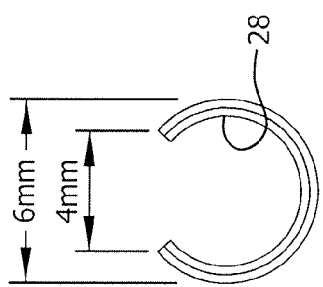
FIG. 1d shows an alternative embodiment of a nasal cannula adapter.
Figure 1G:
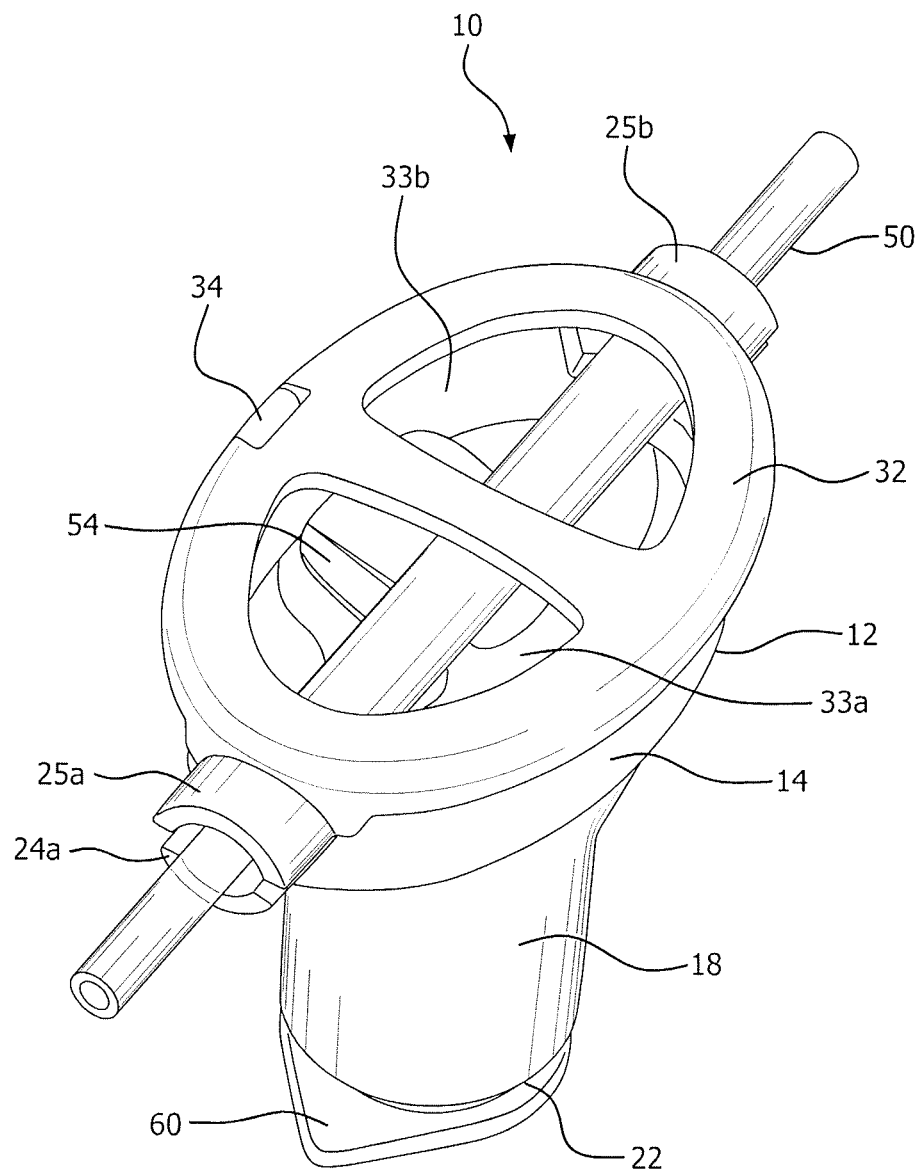
FIG. 1g shows an alternative embodiment of a nasal cannula adapter with a lid.

The chamber 14 of the nasal cannula adapter 10 is preferably open, but in some aspects may be enclosed. Optionally, the nasal cannula adapter 10 may comprise a lid 32 to enclose the chamber 14, as shown in FIG. 1c and in FIG. 1g. The lid 32 may be attached to the body 12, for example, by way of a hinge 34, or may be a separate component of the nasal cannula adapter 10 that may be snapped, screwed, or otherwise fastened in place. The lid 32 may comprise a latch 36. The lid 32 may optionally include a seal 38 to prevent the escape of gas from the chamber 14 through the junction of the lid 32 with the body 12. The lid 32 or enclosed body 12 may include one or more valves, holes, pores, slots, or other openings 33 to allow for exhalation from a patient. FIG. 1g shows an example of two openings 33a and 33b through the lid 32.

Figure 7B:
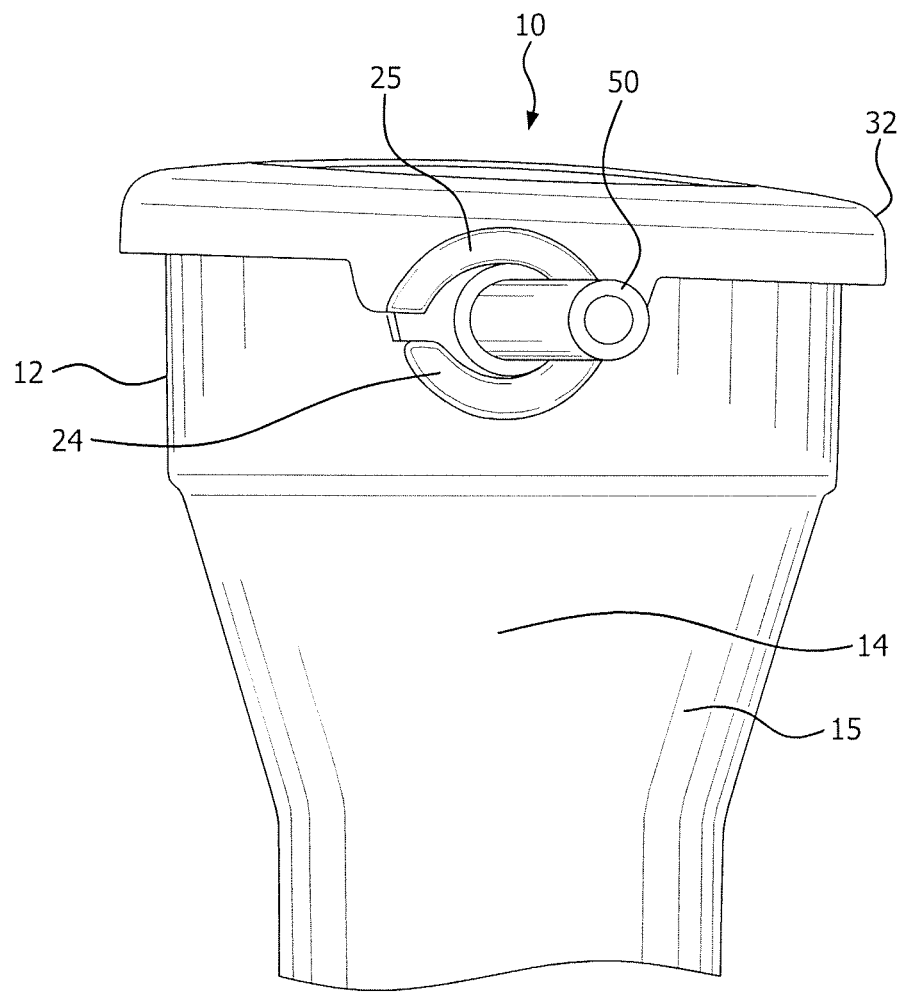
FIG. 7b shows another side view of a nasal cannula adapter and a nasal cannula.

The lid 32 may include lid cannula clips 25 that match up with cannula clips 24 on the body 12. For example, FIG. 1g shows lid cannula clips 25a and 25b extending outward and matching up with the cannula clips 24a and 24b extending outward from the body 12. The lid cannula clips 25 assist in holding a nasal cannula 50 in place in the nasal cannula adapter 10, and allow the lid 32 to close around the nasal cannula 50 without pinching or kinking the nasal cannula 50 (FIG. 7a and FIG. 7b). The lid cannula clips 25a and 25b may comprise a support such as an arm, wing, bracket, branch, protrusion, extension, stirrup, truss, prop, or other support capable of holding and securing the nasal cannula 50 in place on the nasal cannula adapter 10. The lid cannula clips 25a and 25b may be separate and connectable/connected to, or may be integral with the lid 32, and may extend at any suitable angle and in any suitable direction, preferably at an angle and a direction that matches up with the cannula clips 24 on the body 12 (FIG. 1g, FIG. 7a, FIG. 7b). The lid cannula clips 25a and 25b may optionally include a seal 29 (FIG. 7a). Lid cannula clips 25 may also comprise a fastener such as a clasp, clamp, catch, dog, collar, adhesive, grapple, grasp, snare, hook, or other suitable fastener.

Figure 2A:
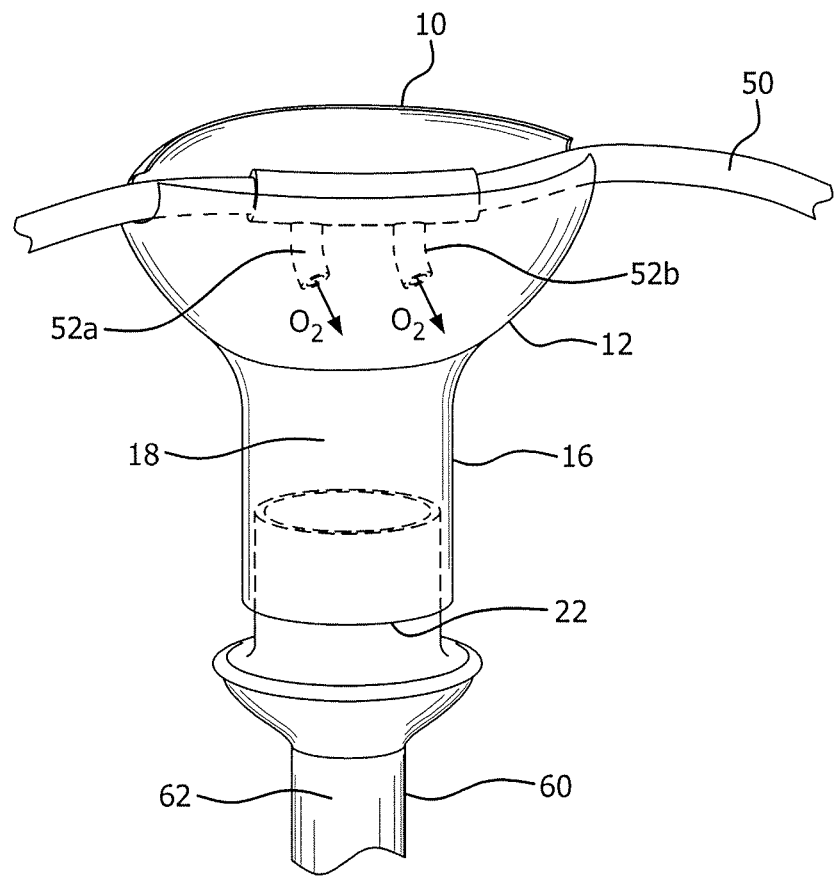
FIG. 2a shows a nasal cannula adapter attached to the external end of an airway device.
Figure 2B:
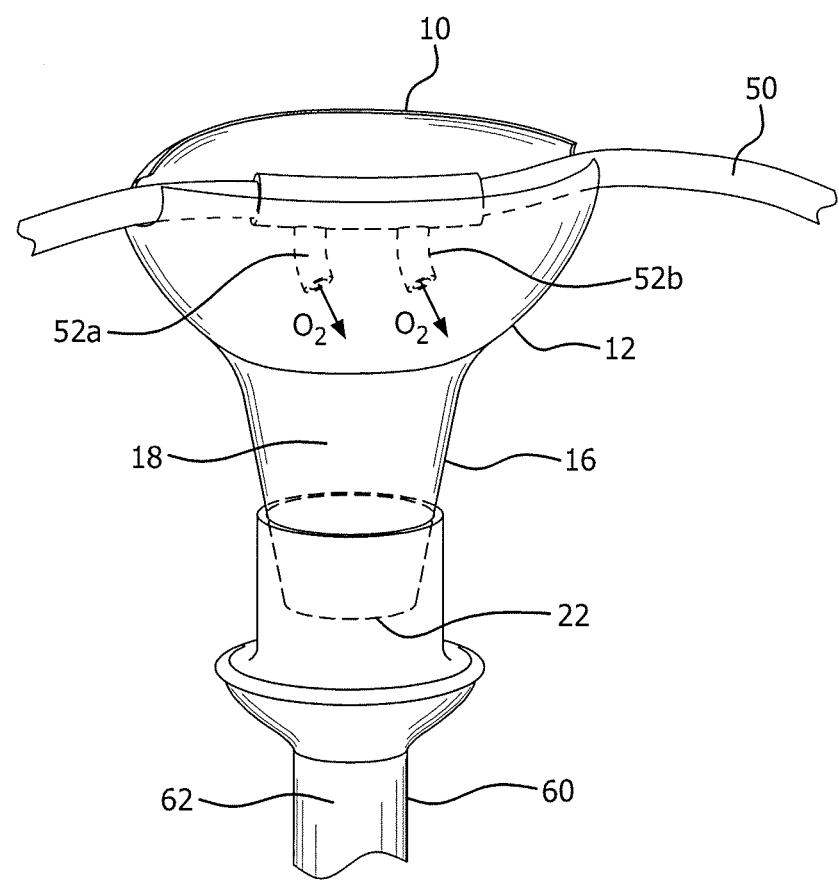
FIG. 2b shows a nasal cannula adapter internally attached to the external end of an airway device.

During operation of the nasal cannula adapter 10, a gas may flow through the nasal cannula 50, for example, in direction A, exit the nasal cannula 50 in direction B through each nare prong 52a and 52b, flow through the chamber 14 and connector lumen 18, and flow into the lumen of an airway device 60 to which the nasal cannula adapter 10 is operably connected (see, e.g., FIG. 1b). As shown in FIG. 2a and FIG. 2b, the gas may be oxygen ($O_2$) as one example (other gases are envisioned). The shape, e.g., tapering, of the inner side wall 15 of the chamber 14 may assist the directional flow of the gas toward the connector lumen 18. If the nasal cannula adapter 10 includes a bulkhead 40, the gas may flow through the nasal cannula 50, exit the nasal cannula 50 through each nare prong 52a and 52b positioned in the holes 42a and 42b of the bulkhead 40, flow into the chamber 14 and into the connector lumen 18, and flow from the connector lumen 18 into the lumen of an airway device to which the nasal cannula adapter 10 is operably connected. In some aspects, the bulkhead 40 may be positioned at or proximal to the junction of the chamber 14 and the connector lumen 18 such that the gas exiting the nare prongs 52a and 52b of the nasal cannula adapter will flow directly into the connector lumen 18, with minimal flow into the chamber 14 save for backflow, if any, through the holes 42a and 42b or other valves, holes, slots, openings, or pores in the bulkhead 40.

The distal end 22 of the connector 16 can be adapted, configured, or shaped to fit over the end of an airway device 60, such as an endotracheal tube, laryngeal mask airway, or tracheotomy tube as shown in FIG. 2a and FIG. 8. Alternatively, the connector 16 can be adapted, configured, or shaped in a funnel shape in order to fit inside of and engage the end of the airway device 60 as shown in FIG. 2b, or can be configured with threads to screw together with the end of the airway device 60. For ease of use, it is preferred that the connector 16 engages the end of the airway device 60 with a friction fit. The end of the airway device 60 to which the connector 16 attaches is the proximal end or external end of the airway device 60, for example, the end of the airway device 60 that remains substantially outside of the patient when the airway device 60 is inserted into the airway of the patient (FIG. 8). Ordinarily, the external end of the airway device 60 would be connected to a gas source, for example, via a tube. The external end of the airway device 60 may comprise a standard fixture 64, connector 64, or adapter 64 that enables the airway device 60 to be operably connected to a gas source 80.

Once the nasal cannula adapter 10 is connected with the airway device 60, the connector lumen 18 is in communication with the lumen 62 of the airway device 60. Thus, when the nasal cannula adapter 10 is in use, a gas may freely flow between the chamber 14, connector lumen 18, and the airway device 60. Optionally, the distal end 22 may have a seal 48 to prevent the escape of gas at the junction between the nasal cannula adapter 10 and the airway device 60.

The nasal cannula adapter 10 and its component parts may have any suitable sizes, shapes, or dimensions. FIGS. 1a and 1d-1f show some non-limiting examples of dimensional aspects of the adapter 10. For example, the body 12 may range from about 3 cm to about 6 cm in width, may range from about 0.5 cm to about 6 cm in height, and may range from about 0.5 cm to about 4 cm in length. In preferred aspects, the body 12 may be about 2.5 cm in height, about 4 cm in width, and about 2.5 cm in length, as shown in FIG. 1e and FIG. 1f. The diameter of the cannula clips 24a and 24b may range from about 0.1 cm to about 1 cm, and the diameter is preferably sufficient to securely hold standard nasal cannula tubing. In some aspects, the diameter of the cannula clips 24a and 24b, which may comprise a support, is about 0.4 cm, and taking into account the thickness of the material used to fabricate the clips 24a and 24b, may be about 0.6 cm (FIG. 1d). In aspects where the cannula clips 24a and 24b are supports, the supports may extend out from the body 12 of the adapter 10 about 0.1 cm to about 1.5 cm, and as shown in FIG. 1e, may extend out from the body 12 about 0.7 cm.

The connector 16 may range from about 1 to about 2.5 cm in height, and the nasal cannula adapter 10 may range from about 3 to about 7 cm in height (FIG. 1a). The width of the opening 20 may be a standard width y designated for fitting together with an airway device. The junction of the body 12 with the connector 16 may comprise any suitable angle, x, which may, for example, be within a range of about 30 degrees to about 70 degrees, inclusive. The junction may have a linear or rounded shape. The dimensions of the height, width, or length of the nasal cannula adapter 10 may be larger or smaller than the dimensions shown in FIG. 1a or FIG. 1d-1f. For example, a smaller nasal cannula adapter 10 may be used with pediatric patients.

Figure 3:
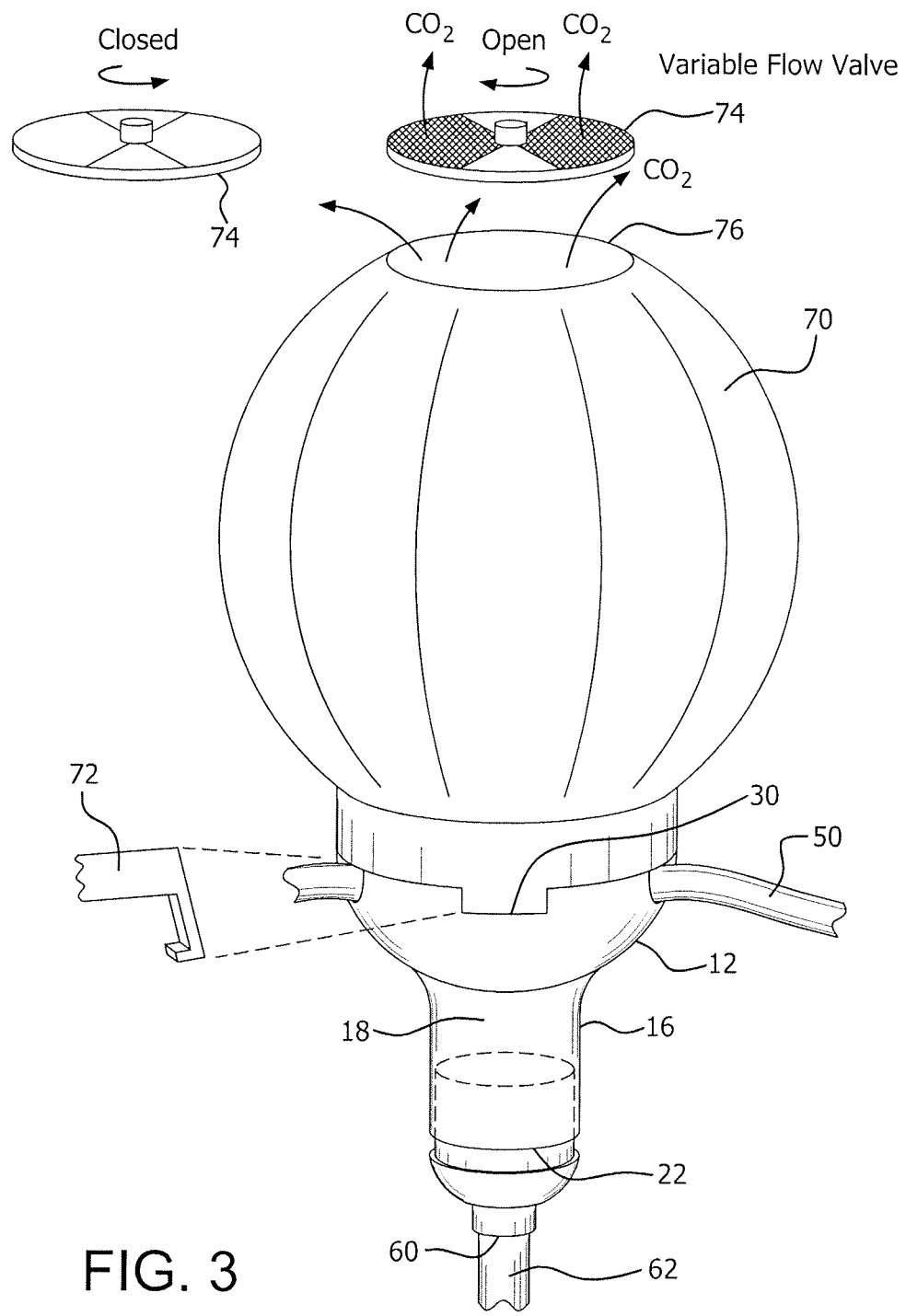
FIG. 3 shows a supplemental oxygen delivery system with an oxygen reservoir.

The nasal cannula adapter 10 may be adapted to attach to an oxygen reservoir 70, as illustrated in FIG. 3. In some aspects, the body 12 of the nasal cannula adapter 10 includes a slot 30 for attaching an oxygen reservoir 70. The slot 30 may be configured for attachment to a portion of the oxygen reservoir 70, which portion may be specifically designed or adapted to mate with the slot 30. In some aspects, the body 12 of the nasal cannula adapter 10 includes a fastener 72 to attach the oxygen reservoir 70 to the nasal cannula adapter 10. Non-limiting examples of suitable fasteners 72 include a clasp, clip, clamp, catch, dog, collar, adhesive, grapple, grasp, snare, hook, or other known fastener. The fastener 72 may, but need not, be integral with the body 12. In some aspects, the body 12 of the nasal cannula adapter 10 does not have any slot 30, fastener 72, or other specialized feature to attach an oxygen reservoir 70. In some aspects, the body 12 of the nasal cannula adapter 10 engages an oxygen reservoir 70 with a friction fit. The oxygen reservoir 70 may include fasteners such as a clasp, clip, clamp, catch, dog, collar, adhesive, grapple, grasp, snare, or hook to enable its attachment to the body 12 of the nasal cannula adapter 10. Oxygen reservoirs 70 may be used, for example, under conditions of high oxygen flow or otherwise where a patient requires higher concentrations of oxygen.

The oxygen reservoir 70 may be any suitable enclosure for containing a suitable volume of oxygen or other gas. Non-limiting examples of suitable enclosures include a balloon, bag, bladder, tube, satchel, box, pouch, or other known vessel or container for containing air. The oxygen reservoir 70 may permit the flow of gas such as carbon dioxide ($CO_2$) exhaled from the patient out from the oxygen reservoir 70. The oxygen reservoir 70 may include a valve 74 to control the flow of a gas such as $CO_2$ out from the oxygen reservoir 70. The valve 74 may be positioned at the proximal end 76 of the oxygen reservoir 70. One non-limiting example of a valve 74 is a retention valve, which can vary the flow of a gas by opening or closing the valve, for example, by rotating the valve.

Figure 4:
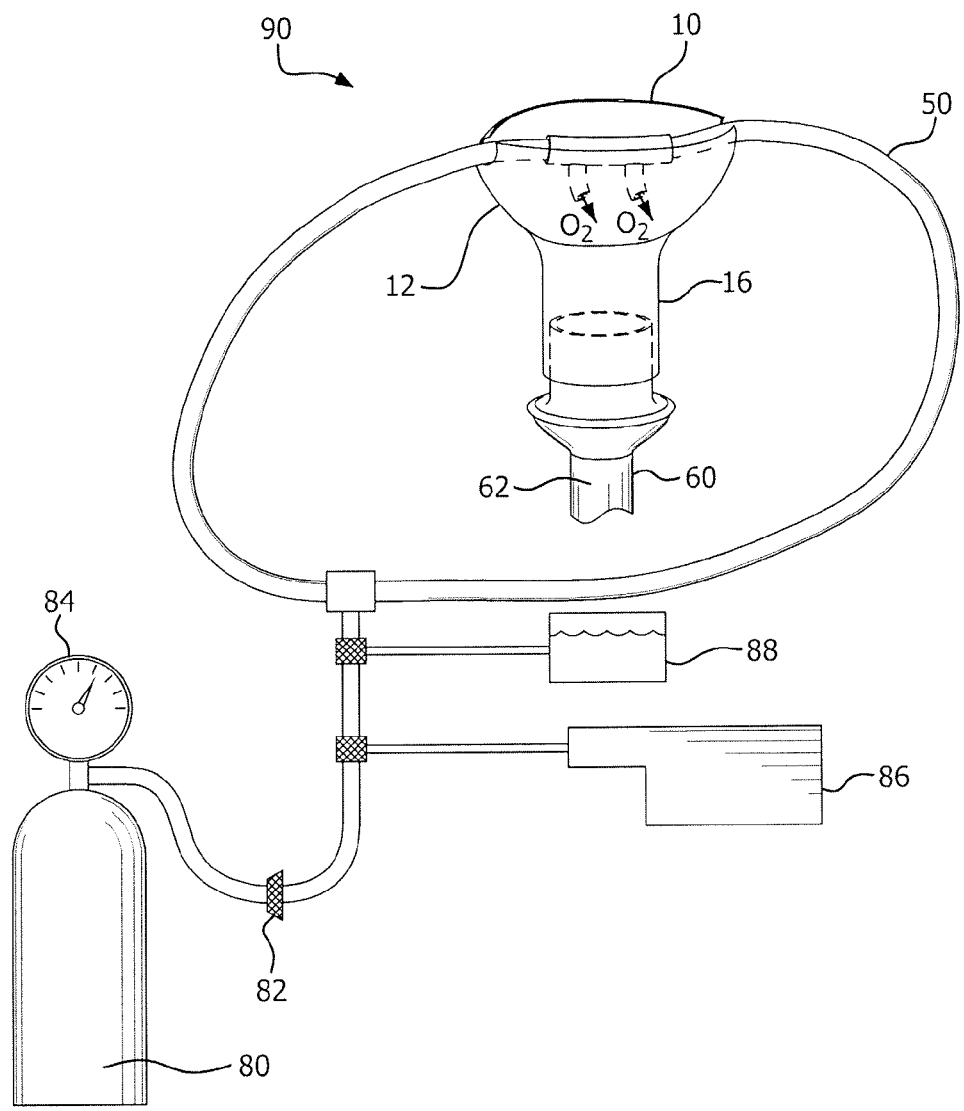
FIG. 4 shows a supplemental oxygen delivery system.

The nasal cannula adapter 10 may be used in accordance with systems for administering a gas to a patient, for example, systems for administering supplemental oxygen to a patient. See, for example, FIG. 4. In some aspects, a system 90 comprises a nasal cannula adapter 10, such as any of the nasal cannula adapters described or exemplified in this document, a nasal cannula 50, an airway device 60, and optionally an oxygen reservoir 70. Suitable airway devices 60 include endotracheal tubes, laryngeal mask airways, combitubes, and tracheotomy tubes, as well as any other known device inserted into a patient's airway to deliver a gas. In some aspects, the system 90 comprises a gas supply 80. The gas supply 80 is preferably an oxygen supply, but may include other gases, for example, anesthetic gases such as nitrous oxide sevoflurane, enflurane, desflurane, isoflurane, and halothane; air; heliox (mixture of helium and oxygen), nitrogen; or combinations of the listed gases. The gas supply 80 may be a wall supply, or a tank, or an anesthesia gas machine. The system 90 may comprise a filter 82; a gas pressure regulator 84; or, as illustrated in FIG. 4, both components. The system 90 may comprise a nebulizer 86 for aerosolizing medications to be administered to the patient, for example, through the nasal cannula 50. The system may comprise a humidifier 88 for adding moisture to the gas being administered to the patient.

The nasal cannula adapters and systems described above can be used, for example, in methods for administering a gas to a patient in need of that gas. The methods comprise administering a gas through a nasal cannula that is operably connected to a nasal cannula adapter that, in turn, is operably connected to an airway device inserted into the airway of the patient. Optionally, the methods may comprise the steps of operably connecting a nasal cannula to a nasal cannula adapter, and/or operably connecting a nasal cannula adapter to an airway device inserted into the airway of a patient. Optionally, the methods may comprise the steps of inserting an airway device into a patient.

In accordance with the methods, the gas can be any suitable medical gas, such as an anesthetic gas, air, nitrogen, heliox, or oxygen, with oxygen being preferred. The nasal cannula may comprise nare prongs. The nasal cannula adapter may be any nasal cannula adapter described or exemplified in this document, and the nasal cannula adapter may include an oxygen reservoir. The airway device may be an endotracheal tube, laryngeal mask airway, combitube, or tracheotomy tube. The methods are suitable for use in any animal, with mammals being preferred, and human beings are most preferred.

The gas can be delivered through the nasal cannula to the patient in any pressure or degree of flow suitable to establish and/or maintain a desired saturation in the patient. By way of example, but not of limitation, suitable flow rates may range from about 0.25 liters per minute to about 15 liters per minute, including from about 0.5 liters per minute to about 10 liters per minute, though greater or lesser flow rates may be used. In some aspects, the methods further comprise removing the airway device from the patient. In some aspects, the methods further comprise removing the nasal cannula from the nasal cannula adapter and placing the nasal cannula on the patient. When placed directly on the patient, the nasal cannula can be used to administer additional gas, preferably oxygen, to the patient.

Although illustrated and described above with reference to certain specific embodiments and examples, the invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges.

I claim:

1. A nasal cannula adapter, comprising a body comprising a chamber, two cannula clips, a connector adapted to connect the nasal cannula adapter to an airway device and having a lumen in communication with the chamber and an opening at a distal end, and a bulkhead positioned substantially where the chamber intersects the lumen, wherein the bulkhead comprises two holes through the bulkhead adapted to friction fit nare prongs of a nasal cannula.

2. The nasal cannula adapter of claim 1, wherein the cannula clips each comprise a support extending outward from the body of the nasal cannula adapter and a hole through the body and extending into the chamber of the nasal cannula adapter.

3. The nasal cannula adapter of claim 2, wherein the cannula clips further comprise a fastener.

4. The nasal cannula adapter of claim 1, wherein the connector is adapted to fit over an end of the airway device.

5. The nasal cannula adapter of claim 1, wherein the connector is adapted to fit inside an end of the airway device.

6. The nasal cannula adapter of claim 1, wherein the connector is adapted to connect the nasal cannula adapter to an airway device selected from the group consisting of an endotracheal tube, laryngeal mask airway, combitube, and tracheotomy tube.

7. The nasal cannula adapter of claim 1, wherein the connector further comprises a seal positioned substantially at the opening.

8. The nasal cannula adapter of claim 1, further comprising a lid attached to the body via a hinge.

9. The nasal cannula adapter of claim 1, further comprising an oxygen reservoir fastened to the body.

10. The nasal cannula adapter of claim 1, wherein the chamber comprises inner side walls shaped to substantially reduce or prevent rotation of a nasal cannula placed in the nasal cannula adapter.

11. The nasal cannula adapter of claim 10, wherein the inner side walls comprise a berm or a ledge configured for contacting a lip plate of a nasal cannula.

12. A system for administering a gas to a patient, comprising the nasal cannula adapter of claim 1, a nasal cannula, and an airway device.

13. The system of claim 12, further comprising a gas supply.

14. The system of claim 12, further comprising a nebulizer.

15. The system of claim 12, wherein the airway device comprises an endotracheal tube, laryngeal mask airway, combitube, or tracheotomy tube.

16. A method for administering a gas to a patient in need thereof, comprising administering a gas through a nasal cannula operably connected to the nasal cannula adapter of claim 1, which is operably connected to an airway device inserted into the airway of the patient.

17. The method of claim 16, wherein the gas is an anesthetic gas or oxygen.

18. The method of claim 16, wherein the gas is administered at a degree of flow suitable to establish or maintain a desired saturation in the patient.

19. The method of claim 16, further comprising removing the nasal cannula from the nasal cannula adapter and placing the nasal cannula on the patient.

20. The nasal cannula adapter of claim 8, further comprising a latch.

* * * * *